(12) United States Patent
Fahl (10) Patent No.: US 11,103,662 B2
(45) Date of Patent: Aug. 31, 2021

(54) COVER FOR A HOUSING OF A MOISTURE-HEAT EXCHANGER

(71) Applicant: Andreas Fahl Medizintechnik—Vertrieb GmbH, Cologne (DE)

(72) Inventor: Andreas Fahl, Cologne (DE)

(73) Assignee: Andreas Fahl Medizintechnik—Vertrieb GmbH, Cologne (DE)

( * ) Notice: Subject to any disclaimer, the term of this patent is extended or adjusted under 35 U.S.C. 154(b) by 252 days.

(21) Appl. No.: 15/564,989

(22) PCT Filed: Apr. 9, 2015

(86) PCT No.: PCT/EP2015/057718
§ 371 (c)(1),
(2) Date: Oct. 6, 2017

(87) PCT Pub. No.: WO2016/162065
PCT Pub. Date: Oct. 13, 2016

(65) Prior Publication Data
US 2018/0071472 A1    Mar. 15, 2018

(51) Int. Cl.
*A61M 16/04* (2006.01)
*A61M 16/10* (2006.01)
*A61F 2/20* (2006.01)

(52) U.S. Cl.
CPC .... *A61M 16/0468* (2013.01); *A61M 16/1045* (2013.01); *A61F 2/20* (2013.01); *A61M 16/0465* (2013.01)

(58) Field of Classification Search
CPC .......... A61M 16/0465; A61M 16/0468; A61M 16/047; A61M 16/1045; A61F 2/20; A61F 2/203
See application file for complete search history.

(56) References Cited

U.S. PATENT DOCUMENTS

| | | | |
|---|---|---|---|
| 4,582,058 A | 4/1986 | Depel et al. | |
| 5,022,394 A * | 6/1991 | Chmielinski | A61M 16/1045 128/206.17 |
| 5,109,471 A * | 4/1992 | Lang | A61M 16/109 392/395 |
| 5,487,382 A * | 1/1996 | Bezicot | A61M 16/047 128/207.14 |
| 6,668,831 B1 * | 12/2003 | Hegwood | A61M 16/0465 128/200.26 |
| 2002/0156527 A1 * | 10/2002 | Persson | A61F 2/20 623/9 |
| 2003/0029456 A1 * | 2/2003 | Lambert | A61M 16/0468 128/207.15 |
| 2009/0050156 A1 * | 2/2009 | Ng | A61M 16/06 128/205.24 |
| 2010/0288284 A1 | 11/2010 | Persson | |
| 2011/0220108 A1 * | 9/2011 | Persson | A61M 16/0468 128/205.29 |

(Continued)

FOREIGN PATENT DOCUMENTS

DE   202013010194 U1   11/2013
EP   2236165 A1   10/2010

*Primary Examiner* — Joseph D. Boecker
(74) *Attorney, Agent, or Firm* — Dinsmore & Shohl LLP (57) ABSTRACT

The invention relates to a cover for a housing of a moisture-heat exchanger for laryngectomized and tracheostomized patients, comprising a cover edge and a number of recesses passing through the cover.

16 Claims, 7 Drawing Sheets

(56) References Cited

U.S. PATENT DOCUMENTS

| | | | |
|---|---|---|---|
| 2012/0090621 A1* | 4/2012 | van der Houwen | ........................ A61M 16/0468 128/207.16 |
| 2013/0192602 A1* | 8/2013 | Leibitzki | ........... A61M 16/0468 128/205.27 |
| 2016/0206846 A1* | 7/2016 | Blom | ................ A61M 16/0468 |
| 2016/0256649 A1* | 9/2016 | Hesselmar | ........ A61M 16/0468 |
| 2018/0071083 A1* | 3/2018 | Fahl | ........................ A61F 2/20 |
| 2018/0256842 A1* | 9/2018 | Fahl | ................. A61M 16/0468 |

* cited by examiner

COVER FOR A HOUSING OF A MOISTURE-HEAT EXCHANGER

CROSS-REFERENCE TO RELATED APPLICATIONS

This application is the U.S. national stage of PCT/EP2015/057718 filed Apr. 9, 2015, of which is hereby incorporated by reference in its entirety.

FIELD OF THE INVENTION

The invention relates to a housing of a moisture-heat exchanger for tracheostomized and laryngectomized patients, comprising a housing cylinder sheath and a filter retention device, as well as a method for releasing a cover from such a housing.

Moisture-heat exchangers for tracheostomized patients are known in general from the prior art. These heat and humidify the inhaled air by means of a filter normally disposed in a cassette or housing. The filter stores the heat and moisture of the exhaled air, and returns it to the inhaled air during inhalation.

BACKGROUND OF THE INVENTION

It is disadvantageous with the known moisture-heat exchangers that it is awkward or difficult to remove potential build-up therefrom. Thus, the PROVOX HME CAP from Atos Medical is known, for example, which can be fitted onto a moisture-heat exchanger filter. This is intended for enabling a closure of the filter, or the tracheostoma, respectively, with the finger, such that it is possible to speak via a voice prosthesis.

The aforementioned slip-on cap comprises a curved titanium ring, which is rigid and has a breathing hole. The disadvantage with the known combination of a filter, or filter cassette, and a cap, is that the moisture-heat exchanger filter is disposed directly below the cap. On one hand, this is disadvantageous visually, and on the other hand, it has the disadvantage that when the breathing hole is closed in order to initiate the speech process, the finger of the user comes in direct contact with the filter, which can lead to contamination. A further disadvantage of the known moisture-heat exchanger is that it is very difficult to remove build-up from the housing, which can lead to difficulties with the use thereof by elderly persons.

SUMMARY OF THE INVENTION

The object of the invention is therefore to overcome the disadvantages known from the prior art, and to provide an improved moisture-heat exchanger for tracheostomized and laryngectomized patients.

The object is achieved according to the invention by means of a cover according to claim 1, a housing according to claim 12, a shield according to claim 16, and a kit according to claim 18. Further advantageous designs can be derived from the following description, the figures, and the dependent claims. The individual features of the various designs are not, however, limited thereto, but rather, can be linked to one another and to other features, to form further designs.

A cover for a housing of a moisture-heat exchanger for tracheostomized and laryngectomized patients is proposed, which comprises a cover edge and a number of holes passing through the cover.

Advantageously, it is provided in one design that the cover can be clamped to a further component of a moisture-heat exchanger, in particular a housing. Furthermore, it is preferably provided that the cover can be screwed or snapped thereon. In one advantageous design it is provided that the cover has clamping elements. The advantage with this design is that it ensures that it is seated securely on the housing, in particular, and at the same time, the production of the moisture-heat exchanger is simplified, in particular with regard to the tool costs.

In one embodiment, it is provided that at least one latching element is disposed on the inner surface of the cover edge.

It is provided in one embodiment that at least one, partially circular, encircling first latching element is disposed on the inner surface of the cover edge. According to one embodiment, the latching element is in the form of a groove. The housing preferably has at least one, likewise circular, encircling latching element, or a circular cover receiver, which interacts with at least the first latching element of the cover. This has the advantage that the cover is disposed in a rotatable manner on the housing. In a further design, the at least one latching element of the housing and the at least one latching element of the cover are designed such that they can be joined in a manner that inhibits rotation. This rotational inhibition is preferably provided by means of a friction.

It is provided in a further embodiment that a number of latching elements are disposed on the inner surface of the cover edge. Preferably, the latching elements are designed as latching lugs or latching projections. In a preferred design, it is provided that the latching elements are raised above the cover edge, facing radially inward, approx. 0.1 mm to approx. 0.9 mm, preferably approx. 0.4 mm to approx. 0.8 mm This design allows for a particularly compact construction.

In a further design, it is provided that the latching elements are distributed about the inner circumference of the cover edge. Preferably, approx. 3 to approx. 20 latching elements, more preferably approx. 6 to approx. 15 latching elements, more preferably 6 or 8 or 9 latching elements, are provided.

The cover preferably comprises a cover surface, or a cover plate, which forms a substantially round disk according to one design. Furthermore, the cover has a cover edge, which extends, particularly preferably, away from the cover plate. In this manner, a cylindrical sheath is formed below the plate, i.e. a cover edge extending toward the housing when in use. The cover edge also preferably encompasses the radial surface of the cover plate.

The first latching element has the form of a bead, latching lug, or projection according to one design. The first latching element can be formed thereby as a continuous round bead on the inner surface of the cover edge. In another design, it is provided that the first latching element comprises a number of beads or projections, which are disposed on the inner surface of the cover edge.

The cover has a number of holes passing through the cover, which enable the user to inhale and exhale sufficient air, and in particular to direct this air through a filter disposed beneath the cover. Advantageously, the cover, in particular the cover plate, has two or more holes. It is particularly preferred that approx. 30% to approx. 90% of the surface of the cover is perforated with holes.

A particularly preferable design is provided in which the holes pass through the cover at approx. 30° to approx. 60°, preferably at approx. 45° to the plane of the cover surface.

The holes, or cut-outs, thus pass through the cover at an angle, or diagonally. This has the advantage that the filter or other devices lying beneath the cover cannot be accessed directly, or cannot be seen, through the holes. It is nevertheless possible for the user to breath reliably and safely through the cover. Another advantage with the embodiment described here is that an attractive design for the user can be obtained. Another advantage of the holes or bores formed at an angle, or diagonally, through the cover is that exhaled air is not directed toward others, in particular in the vicinity of the user. The air can be advantageously deflected downward or to the side through this design. It is also possible to reliably protect the device against spray water with this design.

In a further embodiment, it is provided that at least a portion of the holes are bores. As set forth in the invention, bores are round, circular, or oval holes, which penetrate entirely through the cover, or pass through it, respectively. The bores can be orthogonal to the surface of the cover, or pass through the cover at an angle of approx. 30° to approx. 60°, preferably approx. 45° to the plane of the cover surface. It is provided in a further design, that the holes are disposed in a grid on the surface of the cover. In particular, bores or other types of holes are provided in a grid. Another design provides that the holes have a cross section or diameter that varies over its length. In particular, the holes widen toward the proximal or distal ends thereof. It is likewise particularly preferred that at least a portion of the holes are slits. In another design, it is provided that all of the holes are designed as slits. Further advantageously, the slits are, as specified above, e.g., diagonal or at an angle, and/or provided with a varying cross section.

According to another design, it is provided that slats are disposed between the holes. The holes are advantageously designed as slits. The slits extend over an entire width of the cover according to one design. It is further preferred that the slits are disposed parallel to one another. The slats can be formed, in a further design, through the provision of the slits.

In another design of the cover, it is provided that the cover edge comprises an at least partially encircling second latching element on the outside. The second latching element is designed, in particular, as a fully or partially encircling bead, projection, or other type of projection. Also advantageously, numerous projections are provided, which collectively form the latching element. The second latching element on the outside of the cover edge is provided, in particular, for receiving a shield, in particular a shield that simplifies a closing of the cover, or the respiratory passage, respectively.

In particular, it is provided in one design that the at least one second latching element is provided on the cover, even if the at least one first latching element is not provided on the cover. In a further embodiment, it is provided that the at least one first latching element is provided without a second or further latching element. In another embodiment, it is provided that the at least one first latching element and the at least one second latching element are provided. Furthermore, one embodiment provides that the at least one first latching element and/or the at least one second latching element, and at least one further latching element are provided. The at least one first latching element and/or the at least one second latching element can thus be provided on the cover independently of one another, and disposed on the cover, depending on the requirements by the components connected to the cover.

In another embodiment, it is provided that the shield can be clamped onto the cover. In particular, it is provided according to one design that the shield does not have a latching element. Furthermore, it is provided according to one embodiment that the shield comprises at least one, at least partially encircling bead, in particular for clamping to the cover. Furthermore, one variation of the shield provides that it can be connected to the cover by means of a force fitting and/or form fitting connection.

Furthermore, a housing is proposed, that is to be attached to the cover described above, wherein the housing has a latching element receiver for receiving a first latching element of the cover.

According to one design, it is provided that the cover can be clamped onto the housing.

It is advantageously provided that the cover can be secured to the housing by means of the first latching connection described above, composed in particular of the first latching element of the cover and the latching element receiver of the housing, or at least comprising these individual components. As specified above, it is advantageously provided that the first latching connection is designed such that the cover is disposed on the housing such that it can rotate. Moreover, with this design, a compact construction is obtained.

Furthermore, a shield is proposed that is to be attached to the cover, wherein the shield comprises an at least partially encircling inner latching element receiver for a second latching element of the cover. The cover can preferably be attached to the shield by means of the second latching connection, which comprises at least the second latching element of the cover and the latching element receiver of the shield. The shield is preferably designed such that it has a breathing hole, which is substantially as large as the diameter of the cover. In another design, it is provided that the breathing hole of the shield is approx. 1% to approx. 5% smaller than the diameter of the cover. It is particularly preferably provided that the breathing hole can be disposed centrally over the cover. Furthermore, it is preferably provided in one design that the shield has a recessed, or a funnel, shape surrounding the breathing hole. The funnel shape can be either round or oval, in order to facilitate the placement of the finger thereon in particular. The funnel shaped design is advantageous because it guides the finger to the breathing hole when closing it. The user places the finger on the breathing hole, in order to direct the exhaled air through a voice prosthesis. As a result of the proposed design, it is easier to seal, in particular with a light pressure applied to the shield or the moisture-heat exchanger, necessary for obtaining a sealed closure.

In a particularly preferred design, it is provided that the shield and/or the cover are made of a synthetic rubber, or an elastic material. By way of example, it is provided that the shield and/or the cover comprise a material selected from a group comprising at least a metal, polypropylene and/or polyvinyl chloride. In one design, it is provided that the shield is produced by means of a generative production process, e.g. by means of a 3D printer.

It is provided according to one design that the latching element receiver of the shield has at least one groove, which is preferably at least, preferably entirely, encircling. In particular the at least one groove is C-shaped or L-shaped in a longitudinal section, i.e. in a lateral section from the proximal side. It is further preferably provided that the groove is interrupted once, or multiple times, i.e., the latching element receiver has a number of grooves, disposed adjacently, or it has one groove that encircles it entirely or in part. Advantageously, it is provided according to one design that the second latching element of the cover corresponds to the latching element receiver, in particular the groove, of the shield. This means that the second latching element has the same number of projections, which can engage in the groove or grooves, as grooves provided in the latching element receiver. It is furthermore preferably provided that the groove of the latching element receiver and the projections of the latching element are aligned with one another, in particular such that they fit substantially precisely to one another. The advantage with the designed described here, having an interrupted groove, is that the shield sits on the cover such that it cannot rotate.

A further aspect of the proposed moisture-heat exchanger is a kit comprising at least a number of houses, as described above, a number of covers, as described above, and a number of shields, as described above. The kit is preferably equipped for a moisture-heat exchanger having different housings and/or different covers and/or different shields. The advantage with the proposed kit is that the medical care, or the care with a moisture-heat exchanger, can be individually tailored to the user. The kit is distinguished in particular in that in it is provided in one design that the housings are disposable. This has the advantage that it is not necessary to replace or discard the entire moisture-heat exchanger, but rather, some of the parts can be reused after cleaning, and only the housing needs to be replaced, and in another design, only the filter needs to be replaced. In another design, it is provided that all of the parts of the kit can be reused. In another variation, it is provided that the shields have a number of different colors or shapes. By way of example, the shapes can be substantially round or substantially oval when viewed from above. In further designs, the shields are made of different materials or combinations of materials. In this manner, different elasticities are provided for the various purposes or requirements of the user. In a further design, it is provided that the shields have different breathing holes and/or funnel shapes.

The kit is created in one design such that the covers have a number of differently designed holes. In this manner, holes are provided that have a round or oval cross section. Further designs provide that a further number of holes run straight through the cover, and/or run diagonally or at an angle through the cover.

In a further design, it is provided that the covers have different colors. The kit has the further advantage that not only medically adapted performances can be tailored to the user, but also that the design can be adapted to the preferences of the user.

Furthermore, a housing of a moisture-heat exchanger for tracheostomized and laryngectomized patients is proposed, comprising a housing cylinder sheath. The housing also has a filter retention device, wherein the filter retention device comprises at least one web, dedicated to a base surface of the housing. The housing cylinder sheath has at least three notches, which are designed, in particular, as integral hinges, which enable a defined inward bending of the housing cylinder sheath.

Advantageously, the housing can be used in or on a tracheostoma dressing, a tracheostoma button, and/or a tracheostoma cannula. The housing is preferably cylindrical, wherein a base surface of the housing is formed by the filter retention device. The filter retention device has one or more webs; in particular, it is provided that the webs are interconnected. The housing cylinder sheath also has at least three notches, which are integral hinges in a preferred design. In a further design, it is provided that the notches are designed as predetermined breaking points. The notches are preferably disposed over the housing cylinder sheath such that through pressure, in particular finger pressure, applied to the housing cylinder sheath, it bends inward. An inward bending as set forth in the present invention is understood to mean that the sections of the housing cylinder sheath defined by the notches move toward one another, and, in particular, are pushed radially inward.

The advantage with the housing described herein is that if a cover or other component is disposed on the housing, it can be easily released from the latching connection, in that a pressure, in particular finger pressure, is applied radially to the housing cylinder sheath. The housing cylinder sheath then bends inward in a defined manner, such that it is released from a latching connection to a further component, in particular a cover.

In a preferred design, it is provided that the notches are disposed in relation to one another at an angle of approx. 15° to approx. 75°, more preferably approx. 50° to approx. 70°, more preferably approx. 60°. The arrangement of the notches, and in particular also the number of notches, determines the extent of inward bending, and the resistance exerted by the housing cylinder sheath when pressure is applied to it.

When the term "approx." is used in the framework of the invention, a tolerance range is to be understood therewith, regarded as typical by the person skilled in the art in this field; in particular a tolerance range of ±20%, preferably ±10% is provided for. The term "substantially" also indicates a tolerance range, which is acceptable for the person skilled in the art taking economical and technological aspects into account, such that the feature in question is still recognizable as such.

In another design, it is provided that the notches are disposed on the housing cylinder sheath distributed over an angle of approx. 90° to approx. 180°, preferably approx. 100° to approx. 160°.

In a particularly preferred design, it is provided that the notches are disposed on the inner surface of the housing cylinder sheath. In another design, it is provided that at least one notch is disposed on the outer surface of the housing cylinder sheath. The notches are a thinning of the material, in particular, or a tapering of the cross section of the housing cylinder sheath, disposed on one or both sides of the housing cylinder sheath. Various properties, in particular the bending, can be obtained through the various designs of the notches, e.g. having a triangular cross section or a gentle transition, or a smooth transition to the material thickness of the rest of the housing cylinder sheath. Tensile and pressure forces are formed on the outer and inner surfaces of the housing cylinder sheath through the bending inward, or the exertion of radial forces on the cylinder sheath. These tensile and pressure forces can be defined by the material thinning, or notches, or converted into deformations in a targeted manner In particular, it is provided that the bending inward takes place more easily and over a greater scope than with an equal pressure applied to the housing cylinder sheath without such notches. In one design, in which the notches are designed as predetermined breaking points, the defined breaking of the housing cylinder sheath should be caused, in particular, through a light pressure to the housing cylinder sheath. In particular, the notches are designed such that injuries through sharp edges and/or an uncontrolled breaking, caused by too much force, making it difficult to control the handling thereof, are avoided.

In a further variation of the housing, it is provided that the filter retention device comprises a stop for the inward bending of the housing cylinder sheath. The stop is designed in particular such that the greatest anticipated inward bending is disposed opposite it. The stop is preferably designed such that the housing cylinder sheath is compressed such that either no breaking takes place, or if a breaking in the housing cylinder sheath is intended, it is limited to the region of the notches, in order to avoid a complete breaking.

In the framework of the invention, a predetermined breaking point, or a break, is understood to be a breaking point, as well as a stress whitening breaking point in a plastic part. Stress whitening breaks are small regions that bridge adjacent surfaces with individual, extremely elongated material strands. These extremely elongated material strands are called "crazes," and comprise a preliminary damage to the material.

The filter device can be part of a web, or, preferably, disposed on the web. In particular, the stop is a projection disposed on the web, or formed by a web.

The housing is preferably made from a single material. In another design, it is provided that the housing comprises numerous materials. It is furthermore preferred that the housing is a single piece. In another design, it is provided that the housing comprises numerous pieces. It is particularly preferred that the housing is made of a material selected from a group comprising at least polypropylene and/or polyvinyl chloride. In one design, it is provided that the housing is produced by means of a generative production process, e.g. by means of a 3D printer.

According to another embodiment, it is provided that the filter retention device has a number of webs. The number of webs can be disposed parallel, orthogonal, or in geometric shapes to one another. In particular, it is provided that the webs are disposed radially. The webs have web ends, which, according to one design, are connected to the housing cylinder sheath and/or other webs. According to a particularly preferred design, it is provided that web ends of the webs are distributed over an angle of approx. 180° on an inner circumference of the housing cylinder sheath. This means implicitly that the rest of the cylinder sheath is free of web ends, and the notches for the inward bending can particularly preferably be provided here. Thus, according to one design, it is provided that the housing has a number of webs, wherein web ends are distributed over an angle of 180° on the inner circumference of the housing cylinder sheath, and the housing cylinder sheath has at least three notches, distributed on the other half of the cylinder sheath, which are distributed over an angle of 180°, preferably, however, in an angle of approx. 120°, over the part of the housing cylinder sheath remaining free of web ends.

In a particularly preferred design, it is provided that the housing has a cover receiver for a cover. The cover provides protection for a filter, which on one hand, is intended to prevent the filter from falling out, and on the other hand, is intended to prevent direct visual contact and/or direct physical contact with the filter. The cover is preferably provided with holes. The cover receiver is preferably designed as an at least partially encircling bead, which is disposed on the side of the housing cylinder sheath disposed opposite the filter retention device. The cover receiver, in particular the bead, can have interruptions, or be distributed only on part of the circumference of the housing cylinder sheath. In a further design, it is provided that the cover receiver is disposed on an inner and/or outer circumference of the housing cylinder sheath. It is particularly preferred that the cover receiver is a latching device disposed on the outer surface of the housing cylinder sheath. Because the cover receiver is disposed on the outer surface of the housing cylinder sheath, the latching device of the cover receiver can be pushed out of a latching groove of the cover when the housing cylinder sheath is bent inward through radial pressure applied thereto, and the cover can thus be released from the housing.

It is understood that it is provided in one design that the cover is locked in place on the housing. In particular, a method for releasing a cover from a housing, as described above, is proposed, wherein a force is applied perpendicular to an outer surface of a housing cylinder sheath, in particular in the radial direction thereto, such that the housing cylinder sheath bends inward, in a manner defined by notches, and the cover is released from a latching connection.

Further advantageous designs can be derived from the following drawings. The further developments depicted therein should not, however, be interpreted as limiting, but rather, the features described therein can be combined with one another and with the features described above, to obtain further designs. Moreover, it should be noted that the reference symbols used in the descriptions of the drawings do not limit the scope of protection for the present invention, but refer merely to the exemplary embodiments shown in the figures. Identical parts, or parts having the same function, have the same reference symbols.

DETAILED DESCRIPTION OF THE INVENTION

Figure 1:
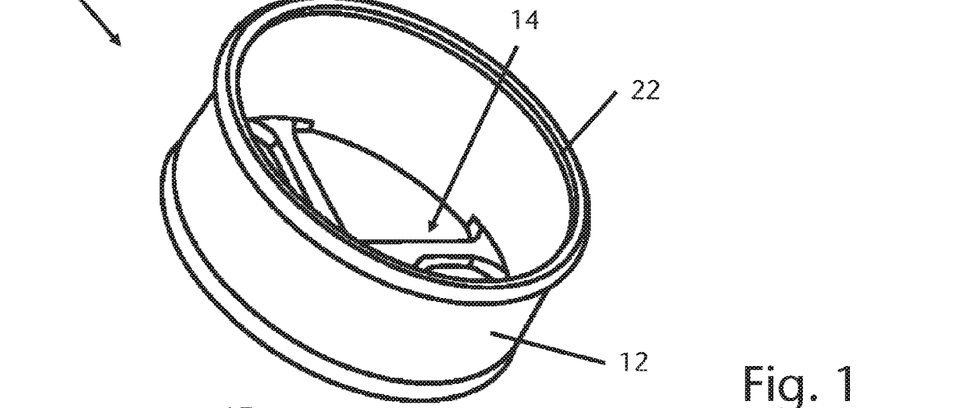
FIG. 1 shows a housing.

FIG. 1 shows a housing 10 of a moisture-heat exchanger for tracheostomized and laryngectomized patients. The housing has a housing cylinder sheath 12, and a filter retention device 14. A filter, not shown, in particular made of an open-cell foam, is inserted in the housing 10, and inserted in a tracheostoma device, e.g. a tracheostoma dressing or a tracheal cannula, such that the filter retention device 14 is proximal to the tracheostoma. The filter retention device 14 prevents a unintentional inhalation of the filter. Furthermore, a cover receiver 22 encircling the outside of the housing cylinder sheath can be seen in FIG. 1, which is designed as a bead on the distal side.

Figure 2:
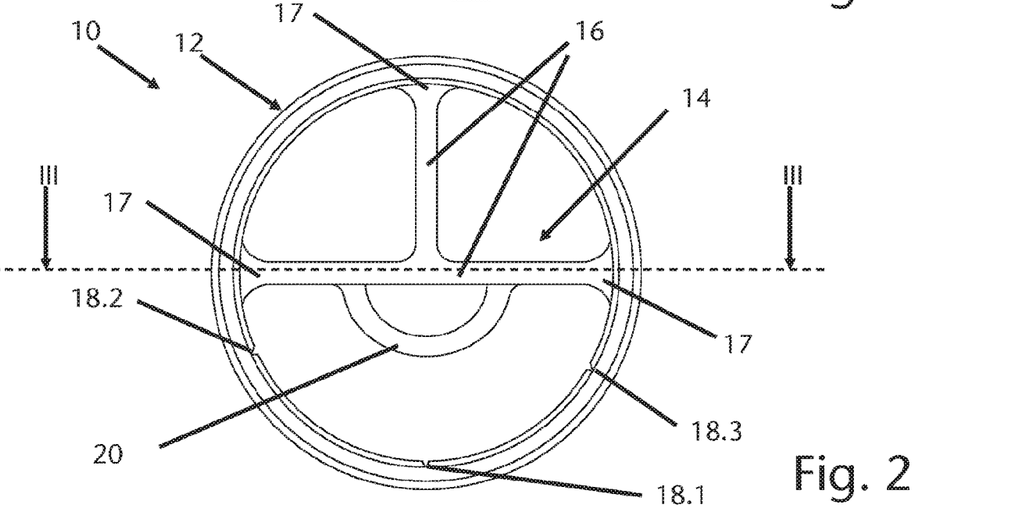
FIG. 2 shows the housing in a top view.

FIG. 2 shows the housing 10 in a top view, wherein the filter retention device 14 can be seen in detail. This has two webs 16 disposed in relation to one another, the web ends 17 of which, lying radially outward, are connected to the inner surface of the housing cylinder sheath 12, or transition into this inner surface. It can be seen that a stop 20 is disposed on one of the webs 16, which forms a circular arc in this design. It can further be seen in FIG. 2 that the housing cylinder sheath 12 has three notches 18, which weaken the housing cylinder sheath 12 in a defined manner A radial pressure applied, for example, to the housing cylinder sheath in the region of the notch 18.1 causes the housing cylinder sheath to bend inward. The defined inward bending is substantially limited in terms of its scope by the notches 18.2 and 18.3. Furthermore, the bending inward is limited by the stop 20, such that an unintentional or excessive deformation, or uncontrolled breaking, does not take place.

Figure 3:
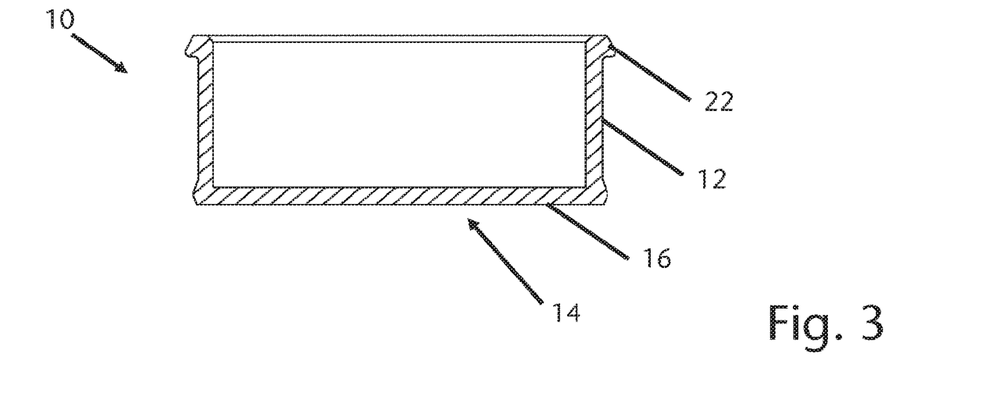
FIG. 3 shows the housing from FIG. 2 in a sectional view.

FIG. 3 shows a sectional view of FIG. 2 at the cut This view likewise shows the housing cylinder sheath 12 as well as the filter retention device 14 with the rib 16. It can furthermore be seen that the housing 10 has a bead on the distal side, which forms the cover receiver 22.

Figure 4:
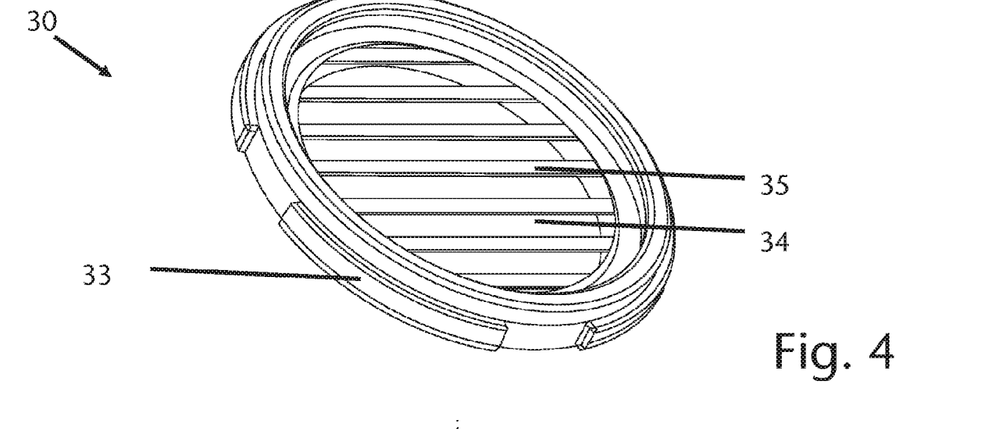
FIG. 4 shows a cover with slats.

FIG. 4 shows a cover 30 for the housing 10 of a moisture-heat exchanger. The cover 30 has a number of holes 34, which are bordered by slats 35. Furthermore, a latching element 33 can be seen in FIG. 4, provided in particular for receiving a shield.

Figures 5, 6:
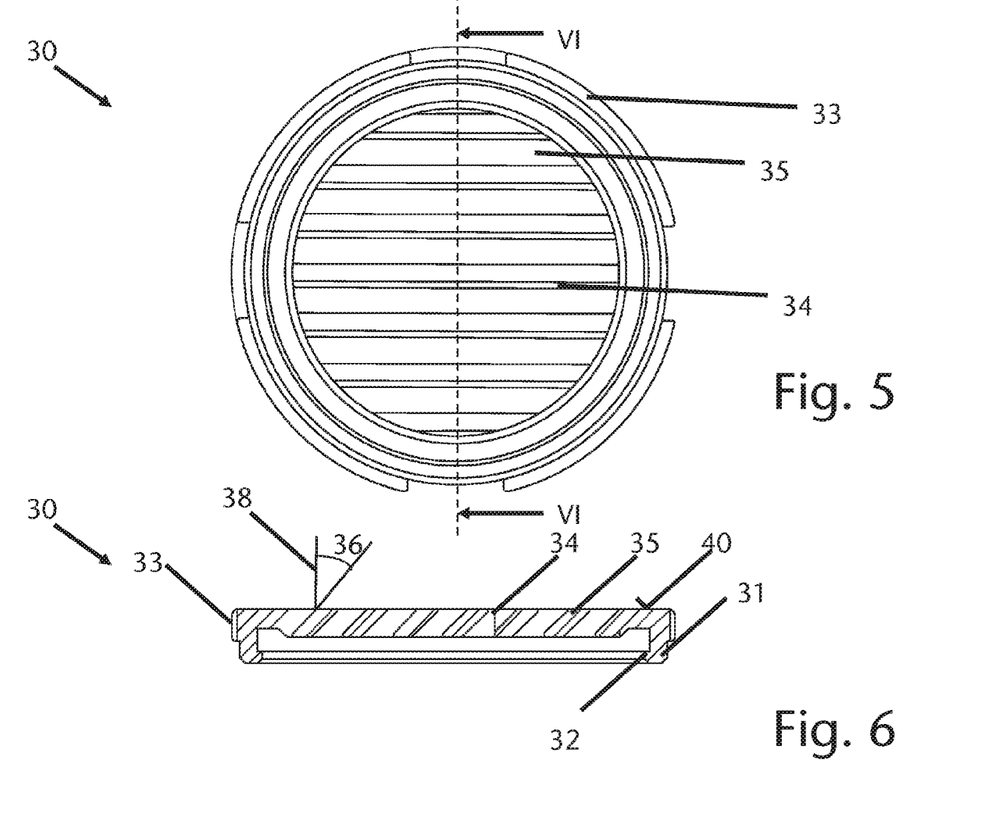
FIG. 5 shows the cover in a top view.
FIG. 6 shows a sectional view of FIG. 5.

FIG. 5 shows the cover 30 from FIG. 4 in a top view. It can be seen that the slats 35 are angled, and the direct view through the holes 35 is relatively narrow, although it can be seen in FIG. 6 that the holes are large enough, even though they pass diagonally through the cover.

As can be seen in FIG. 6, which is a sectional view of FIG. 5 through the cut VI-VI, the holes 34 pass through the cover 30 at an angle 36 of approx. 45° to the plane 38 of the cover surface 40. Furthermore, the partially encircling second latching element 33 can be seen in FIGS. 4 to 6, which encircles the outside of the cover edge 31. As can be seen, for example, in FIG. 6, the cover 30 comprises a cover edge 31, which has a circular first latching element 32 on the inside. This latching element 32 interacts with the cover receiver 22 of the housing to form a first latching connection.

Figure 7:
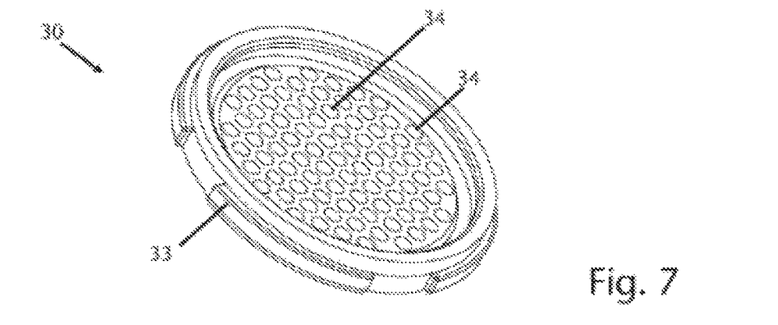
FIG. 7 shows another version of a cover, with bore holes.
Figure 8:
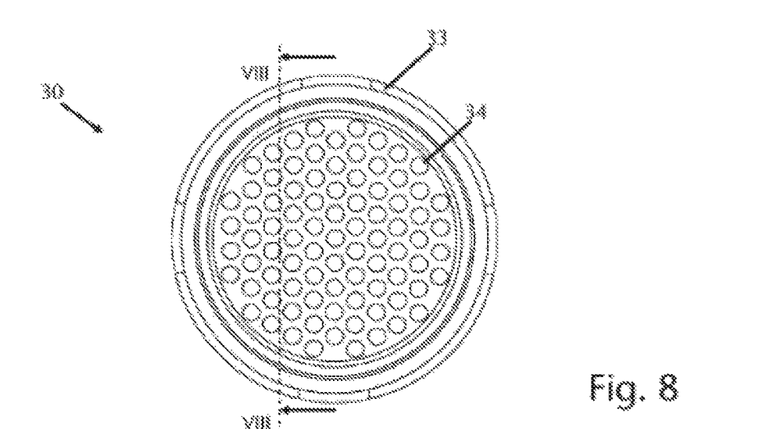
FIG. 8 shows the cover from FIG. 7 in a top view.
Figure 9:
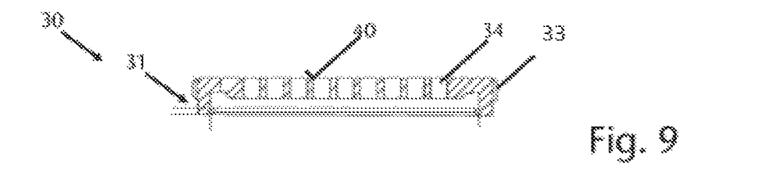
FIG. 9 shows the cover from FIG. 8 in a sectional view.

FIGS. 7 to 9 show a further design of the cover 30, in which the holes 34 are designed as bores. The bores pass through the cover, perpendicular to the surface 40 of the cover 30 in the design shown here.

Figure 10:
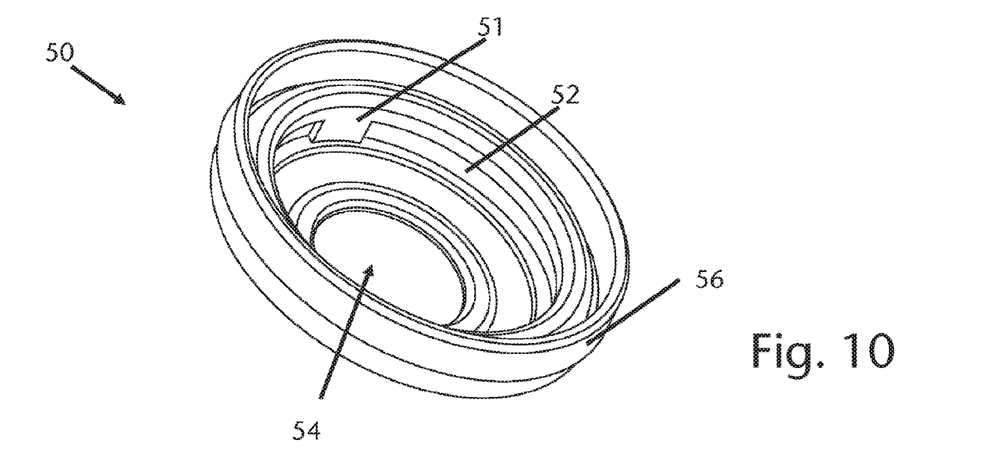
FIG. 10 shows a shield.

FIG. 10 shows a shield 50 that is to be attached to a cover 30. The shield 50 has an at least partially encircling inner latching element receiver 52, which forms a second latching connection with the second latching element 33 of the cover 30. The shield 50 also has a breathing hole 54, which is designed, in particular, such that when it is placed, or has been placed, on the cover 30, the holes remain entirely unobstructed. In this manner, an unimpeded breathing through the assembled moisture-heat exchanger is enabled. The shield 50 has an edge 56 that encompasses the housing 10 and the cover 30, which ensures, in particular, that the housing and the cover, and potential build-up of the tracheostoma dressing, the tracheal cannula, or the tracheostoma button, are not visible. In this manner, the aesthetic demands of a user are satisfied, because the assembled moisture-heat exchanger described thereby also fulfills a decorative function.

Figure 11:
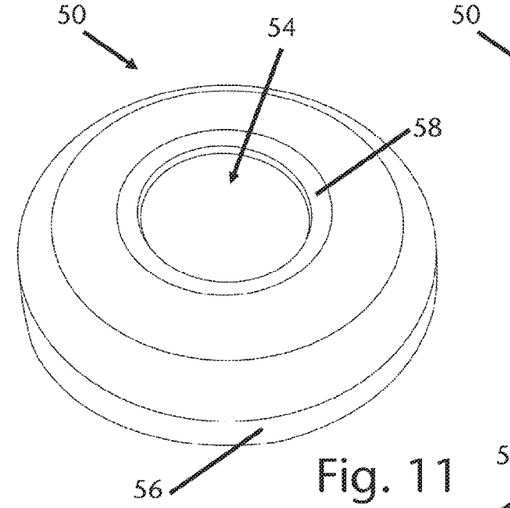
FIG. 11 shows a variation of the shield in a round design.

FIG. 11 shows a variation of the shield 50, wherein the shield 50 has a round, in particular circular, design, in particular in terms of its cross section.

Figure 12:
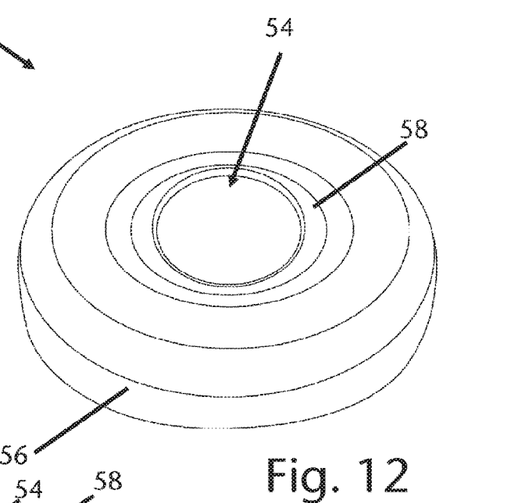
FIG. 12 shows a variation of the shield in an oval design.

FIG. 12 shows a further design of the shield 50, wherein this design has an oval cross section. In particular, the breathing hole 54 has an oval shape.

FIGS. 11 and 12 furthermore show that the breathing hole 54 has a funnel shape. This funnel shape provides, in particular with an intentional closing thereof by the user, a comfortable positioning of the finger on the assembled moisture-heat exchanger.

Figure 13:
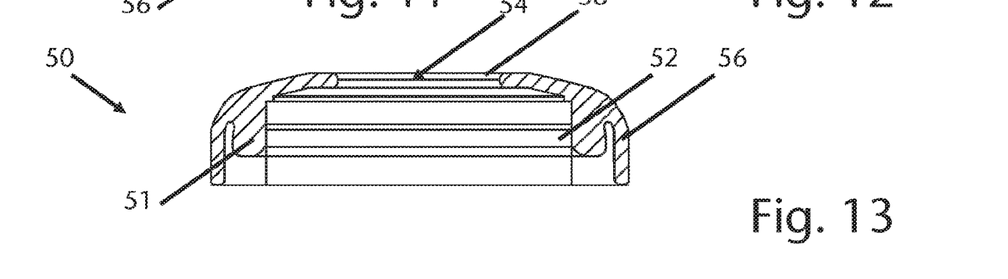
FIG. 13 shows a sectional view of a shield.

FIG. 13 shows a sectional view of a shield 50. The cut passes through the interruptions 51 of the groove of the latching element receiver 52, which can be seen in FIG. 10. The breathing hole 54 as well as the latching element receiver 52 can be seen therein.

Figure 14:
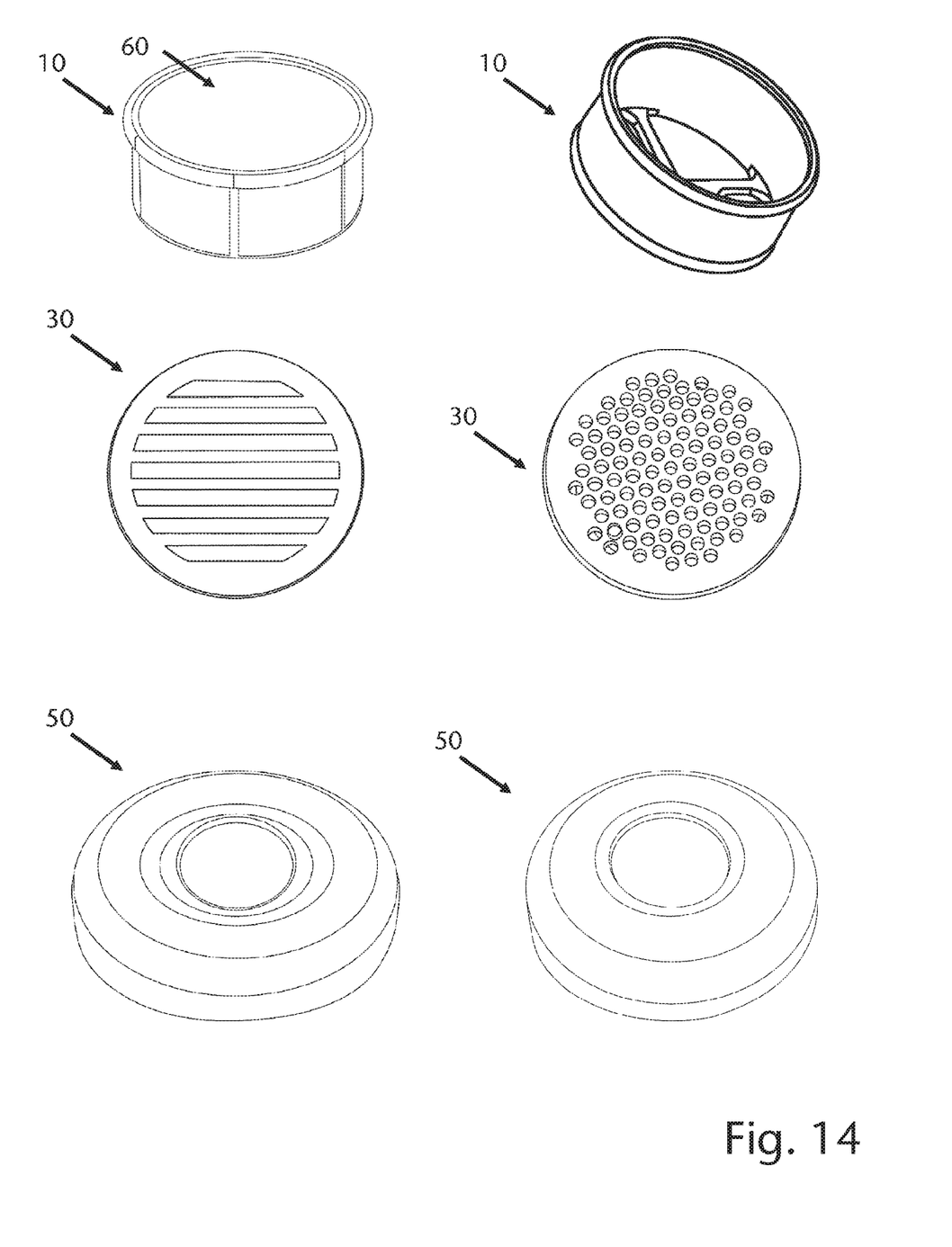
FIG. 14 shows a kit composed of a number of housings, a number of covers, and a number of shields.

FIG. 14 shows a kit for a moisture-heat exchanger. This has a number of housings 10 and a number of covers 30, as well as a number of shields 50. In the example shown here, in each case two variations of the housing 10, the cover 30, and the shield 50 can be seen. A user, or a healthcare provider, e.g. a user's physician, can select the appropriate components for the moisture-heat exchanger. The size of the housing, or the housing receiver in a tracheostoma dressing or suchlike, as well as the intended functionality and the desired design, play a role thereby. It is preferably provided that the housing is designed as a disposable housing. This has a filter 60, supplied separately or directly therewith, which is placed in the housing. After it has been used, or it has been used for a certain period of time, the housing, together with the filter, or just the filter, is replaced. Furthermore, a user can select a cover according to individual preferences, which on one hand, prevents a direct view of the filter, and on the other hand, also prevents the filter from falling out in the distal direction. The cover also has a protective function in that larger particles, dust, or suchlike, and in particular when closing the moisture-heat exchanger, the finger of the user, do not come in direct contact with the filter 60. The user can also choose from a number of shields 50, which in particular, are intended to satisfy an aesthetic demand. Furthermore, the shields also fulfill the technical purpose of making a closing of the moisture-heat exchanger with the finger, for example, comfortable. For this, it is provided that on one hand, the shield 50 is made of a rubber-like material, and on the other hand, the breathing hole 54 is shaped like a funnel.

Figure 15:
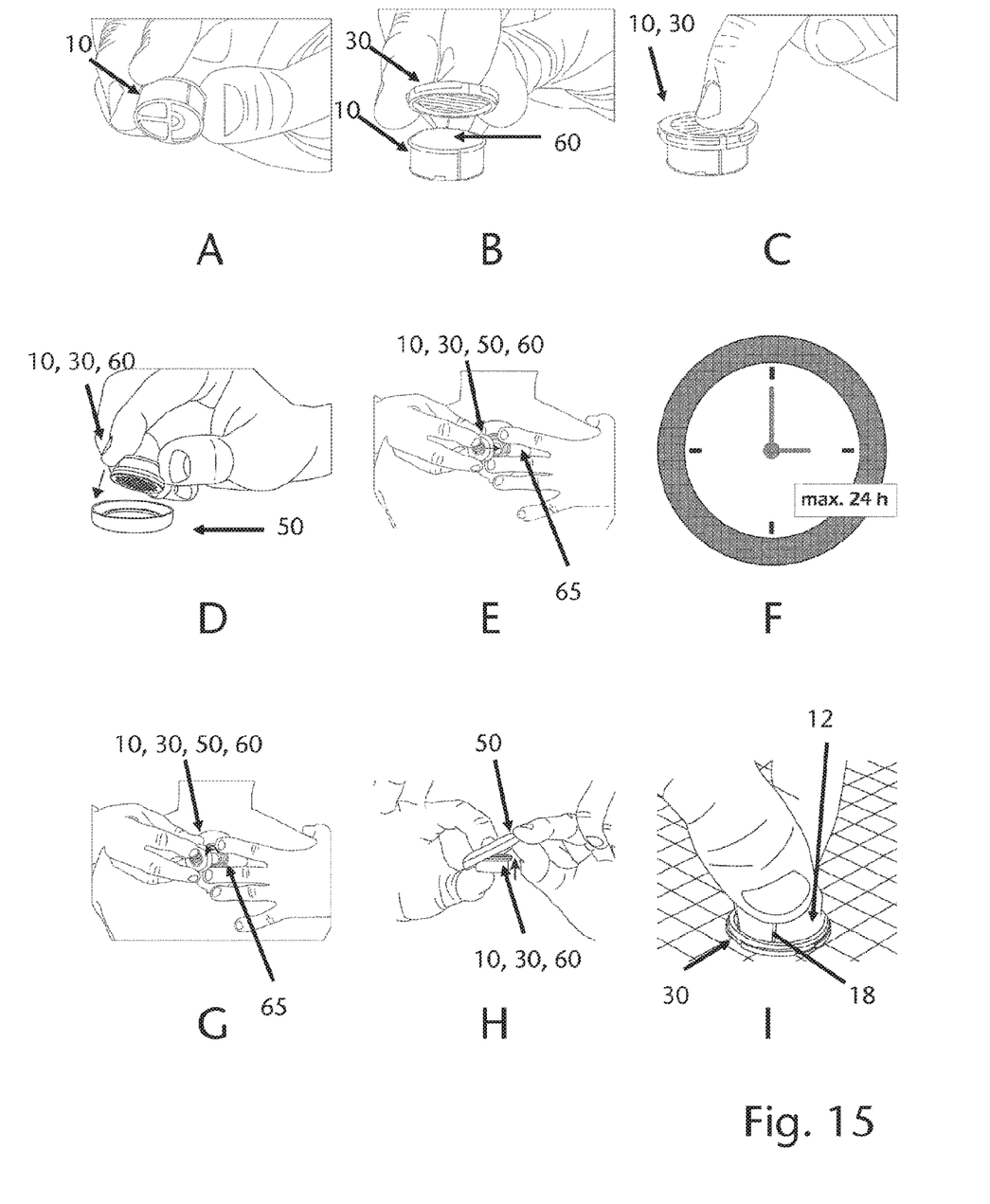
FIG. 15 shows a method for using a moisture-heat exchanger comprising the kit from FIG. 14.

FIG. 15 shows the use of the moisture-heat exchanger described herein, or its kit. Pictogram A shows how a user places the housing 10 on a stable surface. If a filter has not yet been placed in the housing 10, the filter 60 is then inserted, and in the following step, as shown in pictogram B, the cover 30 is placed on the housing 10 and snapped in place. Pictogram C shows that the latching can easily take place by means of finger pressure. The subsequent pictogram D shows that the housing 10 provided with the cover 30 is placed in a shield 50. Here as well, it is proposed that the shield 50 be placed on a stable surface, and the housing 10, including the cover 30, is then pushed into the shield 50. As can be clearly seen in pictogram D, the cover 30 plays a central role here. It engages with both the housing 10 as well as the shield 50. In accordance with a preferred design, it is thus not possible to connect the housing 10 to the shield 50 without the cover 30. The cover 30 thus fulfills a coupling function.

Pictogram E shows that the fully assembled moisture-heat exchanger 10, 30 and 50 is placed in a tracheostoma dressing 65. Pictogram F indicates that the moisture-heat exchanger can be worn for a specific period of time, wherein a maximum period of use of approx. 24 hours is recommended. Depending on the contamination or secretion formation, it may be replaced earlier, or even later. After this time has lapsed, the moisture-heat exchanger is again removed, as shown in pictogram C, and the shield 50 is released from the cover 30. At this point, the housing 10, in particular the housing cylinder sheath 12, is bent inward with a light finger pressure applied to the housing cylinder sheath 12 in the region of the notches 18, until the cover 30 is released form the housing 10.

Figure 16:
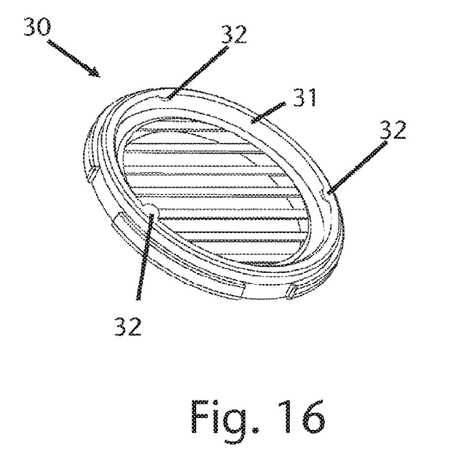
FIG. 16 shows another embodiment of the cover.
Figure 17:
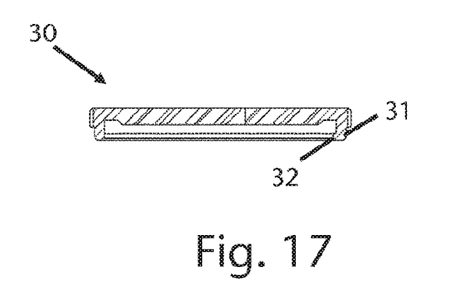
FIG. 17 shows a sectional view of the cover from FIG. 16.

FIG. 16 shows another design of the cover 30 with three latching elements 32, which are disposed on an inner circumference of the cover edge 31, and designed as latching lugs. In order to make the construction as compact as possible, the latching elements 32 are disposed close to the edge, i.e. as proximal as possible to the cover edge. The latching elements 32 extend approx. 0.4 mm to approx. 0.8 mm radially inward. FIG. 17 is a sectional view of the cover 30 from FIG. 16.

Figure 18:
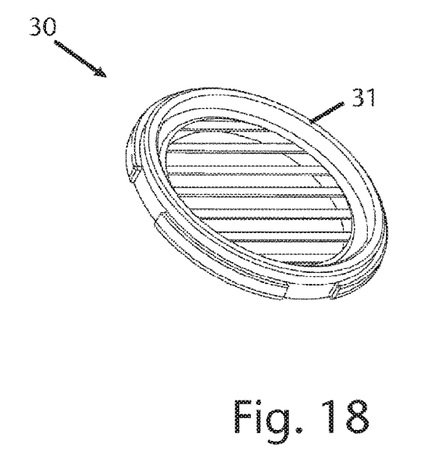
FIG. 18 shows another embodiment of the cover.
Figure 19:
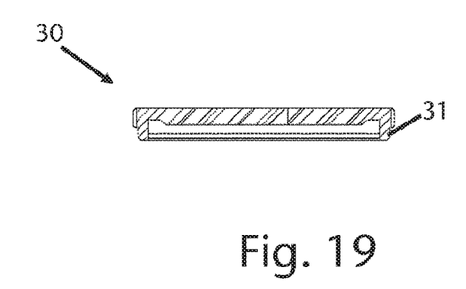
FIG. 19 shows a sectional view of the cover from FIG. 18.

FIG. 18 shows another design of the cover 30 without latching elements 32. This design enables a clamping of the cover 30 onto a housing. FIG. 19 is a sectional view of the cover 30 from FIG. 18.

The invention claimed is:

1. A combination of a shield and a cover for a housing of a moisture-heat exchanger for laryngectomized and tracheostomized patients, the cover comprising a cover edge and a plurality of holes passing through the cover, wherein the shield has a breathing opening;
at least one latching element disposed on an inner surface of the cover edge; and
wherein the cover edge comprises at least a partially encircling second latching element on an outside of the cover edge and wherein the cover edge is attached in a clamping manner to the housing.

2. The combination of a shield and a cover according to claim 1, wherein the at least one latching element is circular and encircling and is disposed on the inner surface of the cover edge.

3. The combination of a shield and a cover according to claim 1, wherein the at least one latching element is distributed over a circumference of the inner surface of the cover edge.

4. The combination of a shield and a cover according to claim 1, wherein each of the plurality of holes pass through the cover at an angle of approximately 30° to approximately 60° to a normal of a plane of a cover surface.

5. The combination of a shield and a cover according to claim 1, wherein at least a portion of the plurality of holes are bore-holes.

6. The combination of a shield and a cover according to claim 1, wherein at least a portion of the plurality of holes are slots.

7. The combination of a shield and a cover according to claim 6, wherein fins are disposed between the slots.

8. The combination of a shield and a cover according to claim 1, comprising the shield having at least a partially encircling inner latching element receiving the second latching element of the cover.

9. The combination of a shield and a cover according to claim 1, wherein the cover is attached to the shield by the second latching element.

10. A combination of a housing and a cover and a shield for a moisture-heat exchanger for laryngectomized and tracheostomized patients, comprising the housing for attachment to the cover having a cover edge and a plurality of holes passing through the cover, the housing comprising a latching element receiver for receiving at least one first latching element of the cover;
wherein the at least one first latching element of the cover is disposed on an inner surface of the cover edge; and
wherein the cover edge comprises at least a partially encircling second latching element on an outside of the cover edge configered to attach to the shield and wherein the cover edge is attached in a clamping manner to the housing.

11. The combination of a housing and a cover and a shield according to cm 10, wherein the cover is rotatable on the housing.

12. A kit for a laryngectomized and tracheostomized patient comprising a plurality of housings, the housings comprising a latching element receiver, a plurality of covers, the covers comprising a cover edge and a plurality of holes passing through the cover;
at least one latching element disposed on an inner surface of the cover edge; and
wherein the cover edge comprises at least a partially encircling second latching element on an outside of the cover edge configured to attach to the shield, and a plurality of shields, the shields comprising at least a partially encircling inner latching element receiver and wherein the cover edge is attached in a clamping manner to the housing.

13. The kit according to claim 12, wherein the housings are disposable.

14. The kit according to claim 12, wherein one of the plurality of shields has a different color and/or shape in comparison to another of the plurality of shields.

15. The kit according to claim 12, wherein the plurality of holes including different shapes in comparison to another of the plurality of covers.

16. The kit according to claim 12, wherein one of the plurality of covers has a different color.

* * * * *